United States Patent [19]

Washington et al.

[11] Patent Number: 5,334,763
[45] Date of Patent: Aug. 2, 1994

[54] PROCESSES FOR MAKING ETHANOLAMINES

[75] Inventors: Samuel J. Washington; Tony F. Grant, both of Baton Rouge, La.

[73] Assignee: The Dow Chemical Company, Midland, Mich.

[21] Appl. No.: 51,719

[22] Filed: Apr. 22, 1993

[51] Int. Cl.$^5$ .................................... C07C 213/04
[52] U.S. Cl. ...................... 564/475; 564/477
[58] Field of Search ...................... 564/475, 477

[56] References Cited

U.S. PATENT DOCUMENTS

| | | | |
|---|---|---|---|
| 2,186,392 | 1/1940 | Ferdinand et al. | 564/477 |
| 3,151,166 | 9/1964 | Milligan | 260/584 |
| 3,849,262 | 11/1974 | Cocuzza | 203/38 |
| 4,169,856 | 10/1979 | Cocuzza et al. | 564/477 |
| 4,355,181 | 10/1982 | Willis, Jr. et al. | 564/477 |

FOREIGN PATENT DOCUMENTS 1210411 8/1986 Canada .
1453762 2/1974 Fed. Rep. of Germany .

*Primary Examiner*—Glennon H. Hollrah
*Assistant Examiner*—Scott C. Rand

[57] ABSTRACT

A process for reducing the amount of the ethoxylated amine byproducts MEAGE, DEAGE and TEAGE formed in a process for making ethanolamines from the reaction of ethylene oxide and ammonia, comprising feeding carbon dioxide or a material which will evolve carbon dioxide to a reactor for conducting such process.

14 Claims, 1 Drawing Sheet

PROCESSES FOR MAKING ETHANOLAMINES

The present invention relates to processes for the manufacture of ethanolamines from ethylene oxide and ammonia.

The materials 2-aminoethanol (or monoethanolamine (MEA)), 2,2'-aminobisethanol (diethanolamine or DEA) and 2,2',2"-nitrilotriethanol (triethanolamine or TEA) are presently commercially produced from ethylene oxide and ammonia (generally as aqueous ammonia) under a variety of conditions. U.S. Pat. Nos. 4,567,303 to Boettger et al., 4,355,181 to Willis et al., 4,169,856 to Cocuzza et al., and Canadian Patent No. 1,210,411 to Gibson et al. are exemplary of the various processes and conditions evidenced in the art.

Common byproducts of these ethanolamines include the corresponding ethoxylated or glycol ether amines, more conventionally referred to as MEAGE (monoethanolamine glycol ether), DEAGE (diethanolamine glycol ether) and TEAGE (triethanolamine glycol ether). These byproducts are undesirable in certain commercial uses of MEA, DEA and/or TEA, and reduce the yield of the desired MEA, DEA and TEA materials.

The present invention is based on the discovery that, in a process for making ethanolamines from the reaction of ethylene oxide and ammonia, the levels of these undesirable ethoxylated amine by-products are reduced or the ethoxylated amine by-products substantially eliminated by feeding even very small amounts of carbon dioxide to the reactor, whether in the form of carbon dioxide gas, solid carbon dioxide or an aqueous ammonium carbonate solution, for example, which will evolve carbon dioxide in the process.

Figure 1:
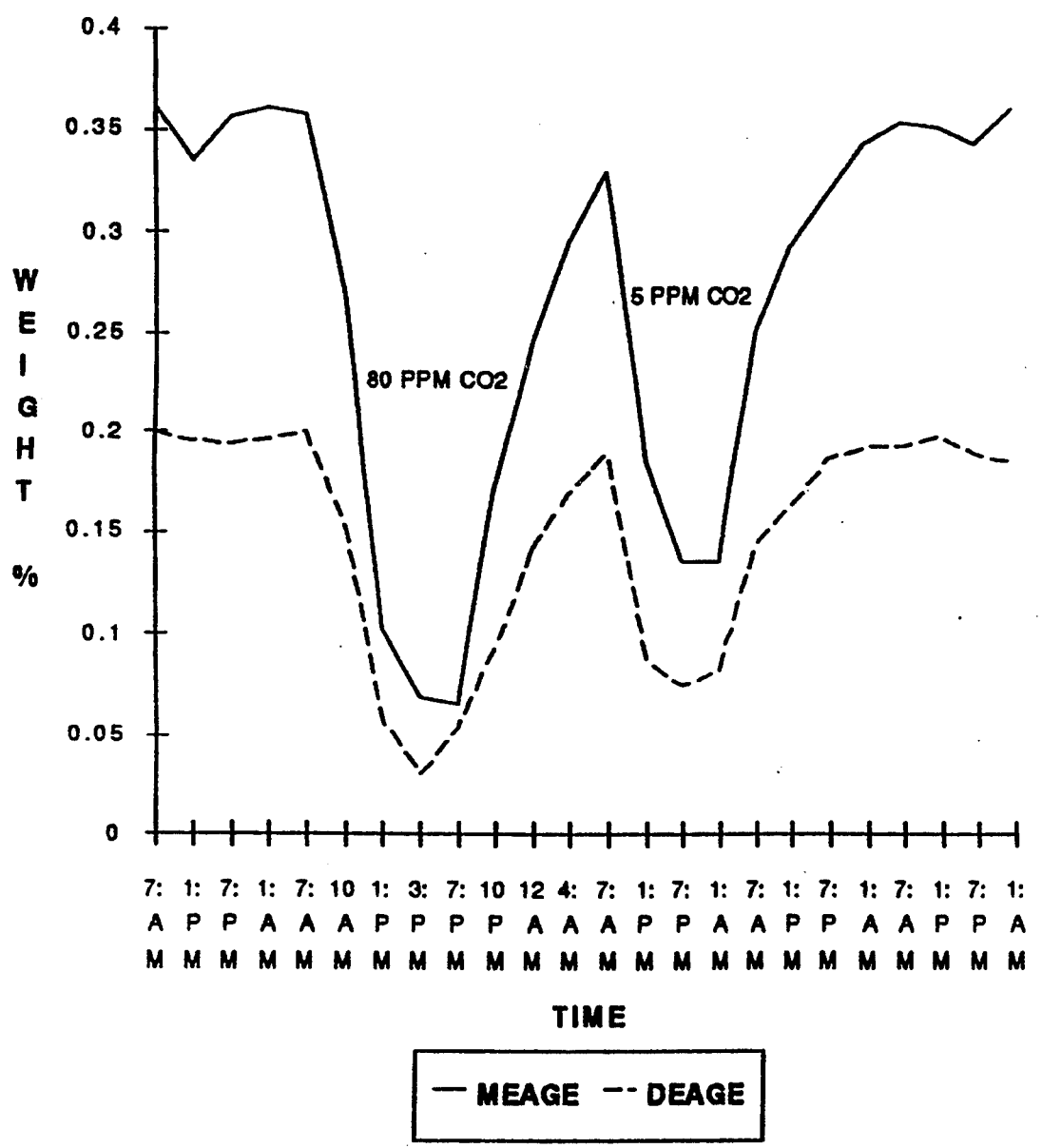
FIG. 1 graphically illustrates the effects of carbon dioxide addition on ethoxylated amine formation in one particular process, as described in Example 2.

In connection with this discovery, it has been determined that the ethoxylated amine byproducts MEAGE, DEAGE and TEAGE are formed through a quaternary ammonium hydroxide salt (tetrakis-2-hydroxyethylammonium hydroxide), which salt has previously been known to be formed by the reaction of triethanolamine and ethylene oxide.

It is presently believed that, according to a mechanism to be described below, carbon dioxide reacts with this quaternary ammonium salt to form a stable carbonate salt before the quaternary ammonium salt can react with MEA, DEA or TEA to form the corresponding ethoxylated amines, so that MEAGE, DEAGE and TEAGE are ultimately formed in significantly lower to negligible amounts.

The quaternary ammonium salt precursor for the MEAGE, DEAGE and TEAGE ethoxylated amine byproducts is stable for reaction temperatures not exceeding about 100 degrees Celsius, and it is in processes conducted at such temperatures that the present invention is most useful. The quaternary ammonium salt is less stable, and therefore less of a problem in terms of ethoxylated amine formation, for processes involving reaction temperatures of from about 100 degrees Celsius up to about 140 degrees Celsius. Even above 140 degrees Celsius, though, some amount of the ethoxylated amine byproducts can be expected to be formed, and it is considered that the present invention is useful in the context of even these higher-temperature processes.

The primary advantage of the present invention, however, is that it permits the reaction of ethylene oxide and ammonia to proceed at much lower temperatures than would otherwise be required to achieve a significant reduction in the levels of the ethoxylated amines as byproducts or their substantial elimination. The product distribution between MEA, DEA and TEA remains basically the same in a process including carbon dioxide addition as compared to a process without carbon dioxide addition.

In the absence of carbon dioxide, it is believed that MEAGE, DEAGE and TEAGE are formed through an endocyclic reorganization of the quaternary ammonium hydroxide salt, substantially as follows:

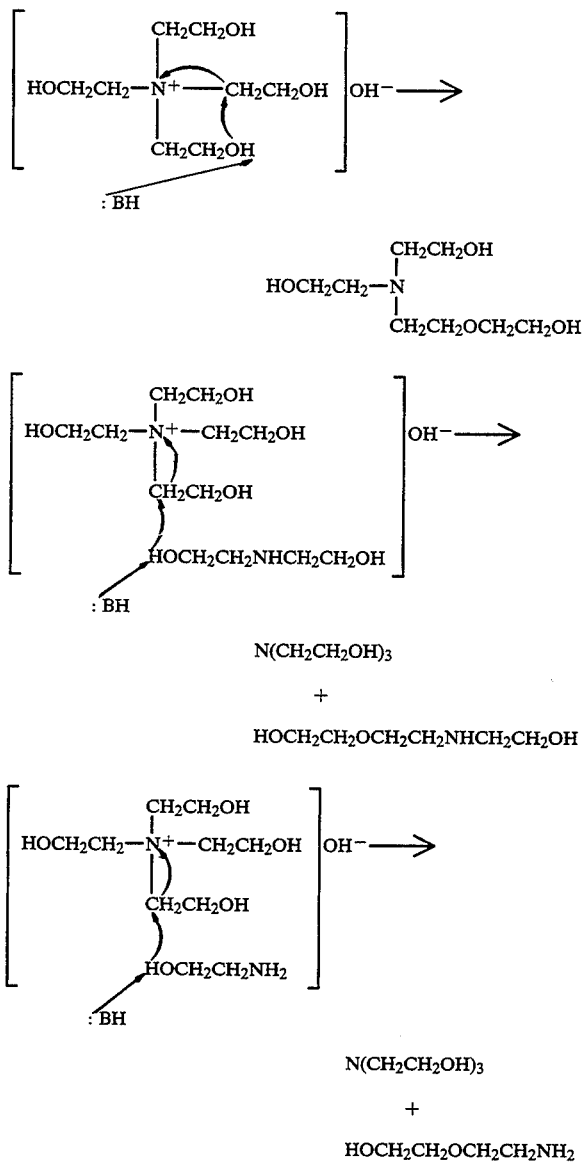

In these reactions, a base (:BH) removes the hydrogen atom in the hydroxyl group of an ethanol on the quaternary ammonium salt of diethanolamine and of monoethanolamine, respectively, and the hydrogen in each of these hydroxyl groups is replaced with an ethanol group from the quaternary ammonium hydroxide salt to correspondingly provide TEAGE, DEAGE and MEAGE. Carbon dioxide appears to reduce the levels of TEAGE, DEAGE and MEAGE which are produced according to these reactions by preferentially replacing the hydrogen which has been removed by the base and forming a stable carbonate salt.

The carbon dioxide, as has been suggested above, can be fed to the process as a gas, as a solid or as a liquid which will evolve carbon dioxide, a preferred liquid being an aqueous solution of ammonium carbonate. In the context of a preferred process for forming ethanolamines from ethylene oxide and aqueous ammonia, the carbon dioxide can be added either to the aqueous ammonia feed or to the ethylene oxide feed, while preferably the carbon dioxide will be added as a solid or as a gas to the aqueous ammonia feed, and most preferably will be added as a gas to the aqueous ammonia feed.

Preferably a sufficient amount of carbon dioxide will be added in one form or another so that the total amount of the MEAGE, DEAGE and TEAGE by-products in the mixed ethanolamines product stream (that is, after removal of ammonia and water) is reduced by at least about 40 percent from the amount produced under the same conditions in the absence of carbon dioxide. More preferably at least about an 80 percent reduction in the total amount produced of MEAGE, DEAGE and TEAGE is achieved, and most preferably a sufficient amount of carbon dioxide is added to realize at least about a 95 percent reduction in these ethoxylated amine byproducts. As a practical matter, it will generally be desirable to add as much carbon dioxide as possible without exceeding the process's ability to handle non-condensable materials.

In a preferred process as described, for example, in U.S. Pat. No. 4,355,181 to Willis, Jr. et al. (such patent being incorporated herein by reference), conventionally from 1 to 3 weight percent of the ethanolamines product stream will be the ethoxylated amine byproducts MEAGE, DEAGE and TEAGE. Through the addition of only enough carbon dioxide to achieve a 5 part per million by weight concentration of carbon dioxide in the ethylane oxide/carbon dioxide feed, it is considered that as much as a 60 percent reduction can be realized in the levels of ethoxylated amines produced. A concentration of from 200 to 300 parts per million by weight in the ethylene oxide feed can typically be expected to result in as much as an 80 percent reduction in the total ethoxylated amines. A presently preferred level of carbon dioxide in this process is 90 parts per million by weight of the total aqueous ammonia and ethylene oxide feed.

At this preferred level, and in one process of the type described in the Willis, Jr. patent, the total ethoxylated amines have been reduced by about 80 percent (to about 0.4 percent by weight of the ethanolamines product stream). In terms of the individual ethoxylated amines, the amount of MEAGE produced has declined from levels of from about 0.35 to about 0.55 percent by weight to in the range of from about 0.10 to about 0.20 percent by weight. The levels of DEAGE produced have declined from about 0.70 to about 0.95 weight percent down to from about 0.08 to about 0.17 weight percent, while TEAGE levels have dropped from about 0.04 to about 0.80 percent by weight down to from about 0.15 to about 0.45 percent by weight. Different reductions can obviously be expected for different processed producing more or less of the TEA material and thus, more or less of the quaternary ammonium salt precursor for the ethoxylated amine byproducts, but it should be a routine matter for those skilled in the art to select an appropriate amount of carbon dioxide to be added in a given process.

The present invention is more particularly illustrated by the following examples:

EXAMPLE 1

For this example, a capillary gas chromatographic analysis was first conducted of the contents of the aqueous ammonia feed tank (other than ammonia and water, both of which were evaporated off before the analysis was conducted) in a commercial ethanolamines production unit, to which DEA was on occasion recycled from a subsequent distillation column for improving TEA yields.

This analysis was conducted, in each instance described below, by preparing a 1:2 mixture by volume of the sample (in this case a feed sample from the aqueous ammonia feed tank) with 2-propanol. This mixture was injected (at 0.5 microliters) into a Hewlett-Packard Model 5890A gas chromatograph employing a 10 meter by 0.32 mm (i.d.) fused silica capillary column coated with a 5-micron film of 5 percent phenyl methyl silicone. The components in the sample were separated and detected via a flame ionization detector, and quantitation was accomplished by peak area calculations using response factors determined from runs of a calibration standard. The amount of water present in the sample was determined using ASTM method E-203.

The oven for the chromatograph was ramped up from 80 deg. C. to 260 deg. C. at 8 deg. C. per minute, and held at 260 deg. C. for 10 minutes. The injection port was set at 300 deg. C., as was the detector. Helium was used as the carrier gas at 1.5 mL/minute and at a 4.5 psig head pressure. The calibration standard employed 2-propanol having known amounts of the various materials of interest (that is, MEA, DEA, TEA, MEAGE, DEAGE and TEAGE) included therein, and response factors were conventionally determined for each of the various components from runs of the calibration standard at the above-referenced conditions.

Results for the sample from the aqueous ammonia feed tank showed the sample included 15.712 percent by weight of MEA, 0.034 percent by weight of MEAGE, 71.098 percent by weight of DEA and 13.156 percent of TEA, with no DEAGE or TEAGE being detected.

As a control, 375 grams of aqueous ammonia (containing MEA, MEAGE, DEA and TEAGE as described in the preceding paragraph, and including 14.34 moles of ammonia) were pressured into a 1 liter Parr reactor which had been modified with a carbon steel jacket to allow controlled heating by a steam/water mixture, and which had been evacuated to thirty (30) inches of mercury for twenty (20) minutes. The reactor was then heated via the mixture of steam and water to a temperature of 86 degrees Celsius, and 251 grams or 5.71 moles of ethylene oxide were pumped into the reactor via a positive displacement pump at 8 to 10 cubic centimeters/minute. Addition of the oxide to achieve the desired 2.5:1 mole ratio of ammonia to oxide required about thirty (30) minutes.

The reactor jacket was maintained throughout at 86 deg. C., while the actual reaction temperature rose to 104 deg. C. as the exothermic reaction proceeded. On subsidence of the exotherm, the reaction temperature was maintained at 86 deg. C. for one additional hour to ensure 100 percent conversion of the oxide. The resulting crude product was then pressured into a 1-liter 316 stainless steel cylinder and the weight of the crude product determined to be 590 grams, or 95 percent accountability. The ammonia in the crude product was allowed to evaporate at room temperature and scrubbed in a 10 percent sulfuric acid solution. Water was removed from the product with a rotary evaporator under vacuum at 100 deg. C., and a capillary gas chromatographic analysis undertaken of the resulting product material. This analysis showed levels of 23.517 percent by weight of MEA in the product material, 0.173 percent of MEAGE, 34.223 percent of DEA, 0.480 percent of DEAGE, 40.215 percent of TEA and 1.392 percent of TEAGE.

The same run was then repeated, except that initially 6.41 grams (0.082 moles) of ammonium carbonate were combined with 37 grams (0.610 moles) of MEA in a capped glass bottle. The ammonium carbonate/MEA mixture was added to the evacuated reactor first, with an additional 10 grams (0.560 moles) of distilled water being added to solubilize any excess carbonate. A capillary gas chromatographic analysis of the product material in this added-carbonate run showed that MEA was present at 27.344 percent by weight, 0.005 percent was MEAGE, 35.955 percent was DEA, 0.011 percent was DEAGE, 36.624 percent was TEA and 0.061 percent was TEAGE.

The results for the feed from the aqueous ammonia tank, for the reaction products in the absence of ammonium carbonate, and for the reaction products in the presence of ammonium carbonate are summarized in terms of weight percents produced of the various materials in Table 1 below, which Table demonstrates that the ethoxylated amines are formed at much lower levels with ammonium carbonate being added than in a conventional process wherein it is not added.

TABLE 1

| Run | MEA | MEAGE | DEA | DEAGE | TEA | TEAGE |
|---|---|---|---|---|---|---|
| Feed Tank | 15.712 | 0.034 | 71.098 | 0 | 13.156 | 0 |
| W/o Ammonium Carbonate | 23.517 | 0.173 | 34.223 | 0.480 | 40.215 | 1.392 |
| W/ Ammonium Carbonate | 27.344 | 0.005 | 35.955 | 0.011 | 36.624 | 0.061 |

EXAMPLE 2

For this example, carbon dioxide was incorporated in the ethylene oxide feed to an aqueous ammonia/ethylene oxide process operating at an ammonia to ethylene oxide molar feed ratio of 2.5 to 1, a pressure of 800 pounds per square inch (gauge), and in a tubular reactor supplied with 8 psig steam (at 86 degrees Celsius) on the shell side of the reactor and reaching a reaction temperature of no more than about 100 degrees Celsius. Two different concentrations of carbon dioxide were employed in the ethylene oxide feed, namely, 80 parts per million by weight of the ethylene oxide/carbon dioxide feed and 5 parts per million by weight of the ethylene oxide/carbon dioxide feed.

The levels of MEAGE and DEAGE produced without carbon dioxide addition and with carbon dioxide addition were monitored over time, using the analytical method described in the preceding example. These levels are shown in FIG. 1 as a function of time for both concentrations of added carbon dioxide, over a period of greater than 4.5 days.

In practice, the ethylene oxide feed to this process was obtained by switching from a first ethylene oxide feed tank containing essentially no carbon dioxide to a second tank containing ethylene oxide and carbon dioxide at 80 ppm by weight. After about thirty minutes, the levels of MEAGE and DEAGE in the mixed ethanolamines product stream began declining. The levels of MEAGE and DEAGE were observed to increase as the feed stream was again switched to the first tank. After the remainder of the $CO_2$-containing ethylene oxide feed in the second tank had been diluted with the addition of pure ethylene oxide to a $CO_2$ concentration of 5 ppm, the feed was again obtained from the second tank and the levels of DEAGE and MEAGE were once again observed to fall.

The process of the present invention is thus well-adapted in its several embodiments to reduce the levels of ethoxylated amine byproducts in the production of ethanolamines from ethylene oxide and ammonia. Those skilled in the art will further recognize that while a number of specific embodiments have been described and/or exemplified herein, still other embodiments and variations are possible and well within the scope and spirit of the present invention, as more particularly defined below.

What is claimed is:

1. A process for reducing the amount of the ethoxylated amine byproducts MEAGE, DEAGE and TEAGE formed in a process for making ethanolamines from the reaction of ethylene oxide and ammonia, comprising feeding carbon dioxide or a material which will evolve carbon dioxide to a reactor for conducting such process.

2. A process as defined in claim 1, wherein the process is conducted at reaction temperatures of less than about 140 degrees Celsius.

3. A process as defined in claim 2, wherein the process is conducted at reaction temperatures of less than about 100 degrees Celsius.

4. A process as defined in claim 1, wherein carbon dioxide is added as a gas to the ammonia feed to the process.

5. A process as defined in claim 1, wherein aqueous ammonia is used as the ammonia feed to the process and carbon dioxide is fed to the reactor as an aqueous solution of ammonium carbonate.

6. A process as defined in claim 1, wherein a sufficient amount of carbon dioxide is fed to the reactor to reduce the amount of MEAGE, DEAGE and TEAGE by at least about 40 percent from the amount of MEAGE, DEAGE and TEAGE formed under the same conditions in the absence of such carbon dioxide.

7. A process as defined in claim 6, wherein a sufficient amount of carbon dioxide is fed to the reactor to reduce the amount of MEAGE, DEAGE and TEAGE by at least about 80 percent from the amount formed in the absence of such carbon dioxide.

8. A process as defined in claim 7, wherein a sufficient amount of carbon dioxide is fed to the reactor to reduce the amount of MEAGE, DEAGE and TEAGE by at least about 95 percent from the amount formed in the absence of such carbon dioxide.

9. A process as defined in claim 4, wherein a sufficient amount of carbon dioxide is fed to the reactor to reduce the amount of MEAGE, DEAGE and TEAGE by at least about 40 percent from the amount of MEAGE, DEAGE and TEAGE formed under the same conditions in the absence of such carbon dioxide.

10. A process as defined in claim 9, wherein a sufficient amount of carbon dioxide is fed to the reactor to reduce the amount of MEAGE, DEAGE and TEAGE by at least about 80 percent from the amount formed in the absence of such carbon dioxide.

11. A process as defined in claim 10, wherein a sufficient amount of carbon dioxide is fed to the reactor to reduce the amount of MEAGE, DEAGE and TEAGE by at least about 95 percent from the amount formed in the absence of such carbon dioxide.

12. A process as defined in claim 5, wherein a sufficient amount of carbon dioxide is fed to the reactor to reduce the amount of MEAGE, DEAGE and TEAGE by at least about 40 percent from the amount of MEAGE, DEAGE and TEAGE formed under the same conditions in the absence of such carbon dioxide.

13. A process as defined in claim 12, wherein a sufficient amount of carbon dioxide is fed to the reactor to reduce the amount of MEAGE, DEAGE and TEAGE by at least about 80 percent from the amount formed in the absence of such carbon dioxide.

14. A process as defined in claim 13, wherein a sufficient amount of carbon dioxide is fed to the reactor to reduce the amount of MEAGE, DEAGE and TEAGE by at least about 95 percent from the amount formed in the absence of such carbon dioxide.

* * * * *